(12) United States Patent
Mros et al.

(10) Patent No.: US 8,092,409 B2
(45) Date of Patent: Jan. 10, 2012

(54) REINFORCED CONNECTOR

(75) Inventors: Henry Mros, Taunton, MA (US); Peter Martin, Assonet, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 1271 days.

(21) Appl. No.: 11/750,452

(22) Filed: May 18, 2007

(65) Prior Publication Data

US 2008/0287843 A1    Nov. 20, 2008

(51) Int. Cl.
*A61H 23/00* (2006.01)
*A61F 5/00* (2006.01)

(52) U.S. Cl. ............. 601/151; 601/152; 285/124.2; 285/124.4; 285/124.5

(58) Field of Classification Search .......... 601/148, 601/149, 150, 151, 152; 602/13; 403/13; 606/201, 202; 128/DIG. 20; 285/124.1–124.5, 285/26, 93, 304, 305, 317, 319, 914, 921
See application file for complete search history.

(56) References Cited

U.S. PATENT DOCUMENTS

| | | |
|---|---|---|
| 369,813 A | 9/1887 | Rader |
| 1,181,481 A | 5/1916 | Robinson |
| 1,578,368 A | 3/1926 | Robinson |
| 1,936,015 A | 11/1933 | Harrell |
| 2,628,850 A | 2/1953 | Summerville |
| RE29,054 E | 11/1976 | Lange |
| 4,253,449 A | 3/1981 | Arkans et al. |
| 4,280,485 A | 7/1981 | Arkans |
| 4,378,124 A | 3/1983 | Weirich et al. |
| 4,478,436 A | 10/1984 | Hashimoto |
| 4,801,162 A | 1/1989 | Rozycki |
| 4,804,208 A | 2/1989 | Dye |
| D333,293 S | 2/1993 | Ashida |
| 5,219,185 A | 6/1993 | Oddenino |
| 5,234,185 A | 8/1993 | Hoffman et al. |
| 5,236,227 A | 8/1993 | Adams et al. |
| D357,736 S | 4/1995 | Dye |
| D363,988 S | 11/1995 | Dye |
| D364,459 S | 11/1995 | Dye |
| D364,460 S | 11/1995 | Dye |
| 5,478,119 A | 12/1995 | Dye |
| D373,191 S | 8/1996 | Ribando et al. |
| D373,192 S | 8/1996 | Murphy et al. |
| 5,588,954 A | 12/1996 | Ribando et al. |
| 5,662,500 A | 9/1997 | Yeah |
| 5,725,485 A | 3/1998 | Ribando et al. |

(Continued)

FOREIGN PATENT DOCUMENTS

GB    2373444 A    9/2002

*Primary Examiner* — Quang D Thanh
(74) *Attorney, Agent, or Firm* — Thomas M. Johnston, Esq.

(57) ABSTRACT

A connector for attaching a flexible tube to a fluid passage of another object includes a housing and a connector port on the body. The connector port is sized and shaped for connecting the connector port in fluid communication with the fluid passage of the object. The connector includes a tube port projecting from the body. The tube port is adapted for fluid communication with the connector port and is sized and shaped for being received in an end of the flexible tube to establish fluid communication with the flexible tube. The tube port includes a tube retainer that projects from the body toward the tube port. The retainer has an engaging end portion disposed in relation to the tube port to engage the flexible tube when the tube port is received in the flexible tube. The flexible tube is restrained from lateral movement with respect to the tube port.

33 Claims, 12 Drawing Sheets

U.S. PATENT DOCUMENTS

| | | |
|---|---|---|
| D396,695 S | 8/1998 | Shen |
| 5,951,059 A | 9/1999 | Kitamura |
| 6,062,244 A | 5/2000 | Arkans |
| D460,046 S | 7/2002 | Wood |
| D460,417 S | 7/2002 | Wood |
| RE38,204 E | 7/2003 | Kazarian |
| 6,802,855 B2 | 10/2004 | Ellingboe et al. |
| 6,827,728 B2 | 12/2004 | Ellingboe et al. |
| 6,871,878 B2 | 3/2005 | Miros |
| 6,926,311 B2 | 8/2005 | Chang et al. |
| D516,514 S | 3/2006 | Chau et al. |
| 7,163,531 B2 | 1/2007 | Seese et al. |
| 2005/0143682 A1 | 6/2005 | Cook et al. |
| 2005/0184264 A1 | 8/2005 | Tesluk et al. |

REINFORCED CONNECTOR

TECHNICAL FIELD

This invention relates to connectors for attaching flexible tubes, particularly for use for attaching flexible tubes of medical apparatus including compression therapy devices and air pumps.

BACKGROUND OF THE INVENTION

In a medical environment, many devices have a fluid connection to other devices or to a patient that is made by flexible tubing. One example is the connection of an air compressor to an inflatable bladder in a compression device used in deep vein thrombosis therapy. When connecting a medical device to a fluid supply, a non-leaking seal must be made between compatible devices and/or fluid sources. Thus, connections must be designed to provide an adequate seal between sealing surfaces when the devices and/or supply are compatible. Typical devices have a male and female connector that, when pressed together, form a fluid tight seal. The connectors come in different sizes and shapes and typically have ports, O-rings or gaskets to help create a fluid tight seal.

Typical compression therapy devices are wrapped around a limb to prevent peripheral edema and conditions such as deep vein thrombosis. These devices typically include at least one air bladder that is sized and shaped for being applied on or around the limb. The bladder is sequentially inflated and deflated to artificially stimulate blood flow throughout the appendage that would normally result from, for example, walking.

An example of such a device that is configured for disposal about a foot is shown in U.S. Pub. No. 2005/0187499 and a device configured for disposal about the leg is shown in U.S. Pub. No. 2005/0187503. Typically, these compression therapy devices are connected to a tube set which provides fluid communication from a pressure source (e.g., an air compressor) to the compression therapy device. A controller is employed to regulate the flow of fluid from the pressure source to the compression therapy device.

The compression therapy device, tube set and controller each contain connections for connecting and disconnecting the compression therapy device from the pressure source. Often the compression therapy device includes a plurality of bladders and separate tubes for independently inflating each bladder. The connectors include a plastic housing having at least one tube port for connecting to a tube and, in many instances include a plurality of tube ports. The housing is more rigid than the flexible tubing, and also is capable of being connected via a mating connector to other tubes or to the controller.

Typically the tube ports of the connectors are received within the tubes. During disconnection of mating male and female connectors, the practitioner often grasps the tubes and pulls such that the male and female connectors become separated. This causes bending forces to be applied to the tube ports that result in one of the tube ports breaking off from the housing of the connector. This is particularly a problem with connectors that attach to controllers of sequential compression devices as the controller is typically stationary and the connectors are not at the same height as the practitioner.

Hashimoto, U.S. Pat. No. 4,478,436 shows a hose clam shell style sleeve that fits around tubes that are connected to a fitting. The tubes fit in semicircular slots in the sleeve. The separate sleeve is not practical in use and may be come easily lost. Dye, U.S. Pat. No. 4,804,208, shows a connector that has a narrow slot in a cover through which the tubes project into the connector for attachment to ports. The cover is also a separate part that may become lost.

SUMMARY OF THE INVENTION

In one aspect, a connector for attaching at least one flexible tube to a fluid passage of another object generally comprises a body, and at least one connector port on the body sized and shaped for connecting the connector port in fluid communication with the fluid passage of the object. The connector further includes at least one tube port projecting from the body adapted for fluid communication with the connector port. The tube port is sized and shaped for being received in an end of the flexible tube to establish fluid communication with the flexible tube. The connector includes a tube retainer projecting from the body toward the tube port. The tube retainer has an engaging end portion disposed in relation to the tube port to engage the flexible tube when the tube port is received in the flexible tube. The tube retainer restrains the flexible tube from lateral movement with respect to the tube port.

In another aspect, a compression system for use in applying pressure to an appendage of a patient generally comprises an air pump for supplying air under pressure. The air pump includes a fluid passage. The system includes at least one flexible tube and a connector adapted for attachment to the outlet of the air pump and for attaching at least one flexible tube to a fluid passage of another object. The connector comprises a body and at least one connector port on the body sized and shaped for connecting the connector port in fluid communication with the fluid passage of the air pump. The connector includes at least one tube port projecting from the body adapted for fluid communication with the connector port. The tube port is sized and shaped for being received in an end of the flexible tube to establish fluid communication with the flexible tube. The connector includes a tube retainer projecting from the body toward the tube port. The tube retainer has an engaging end portion disposed in relation to the tube port to engage the flexible tube when the tube port is received in the flexible tube. The retainer restrains the flexible tube from lateral movement with respect to the tube port.

In yet another aspect, a compression therapy device for use with a source of air pressure having a fluid passage generally comprises at least one air bladder sized and shaped for being applied to an appendage of a patient. The air bladder is in fluid communication with a flexible tube. A connector is connected to the tube. The connector comprises a body and at least one connector port on the body sized and shaped for connecting the connector port in fluid communication with the fluid passage of the source of air pressure. The connector includes at least one tube port projecting from the body adapted for fluid communication with the connector port. The tube port is sized and shaped for being received in an end of the flexible tube to establish fluid communication with the flexible tube. The connector includes a tube retainer which projects from the body toward the tube port. The tube retainer has an engaging end portion disposed in relation to the tube port to engage the flexible tube when the tube port is received in the flexible tube. The retainer restrains the flexible tube from lateral movement with respect to the tube port.

Other features will be in part apparent and in part pointed out hereinafter. Various refinements exist of the features noted in relation to the above-mentioned aspects of the present invention. Further features may also be incorporated in the above-mentioned aspects of the present invention as well. These refinements and additional features may exist individually or in any combination. For instance, various features discussed below in relation to any of the illustrated embodiments of the present invention may be incorporated into any of the above-described aspects of the present invention, alone or in any combination.

BRIEF DESCRIPTION OF THE DRAWINGS

Corresponding reference characters indicate corresponding parts throughout the drawings.

DETAILED DESCRIPTION OF THE DRAWINGS

Figure 1:
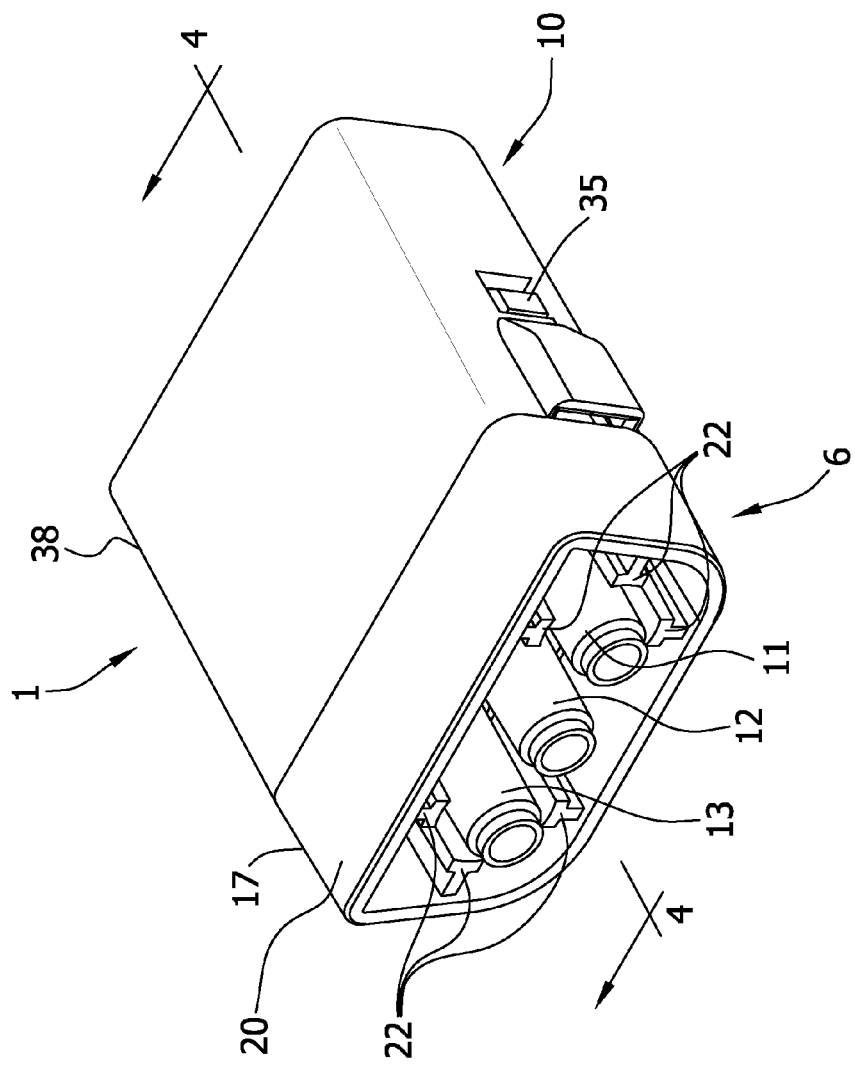
FIG. 1 is a perspective of a connector apparatus with first and second connectors of the connector apparatus engaged.
Figure 2:
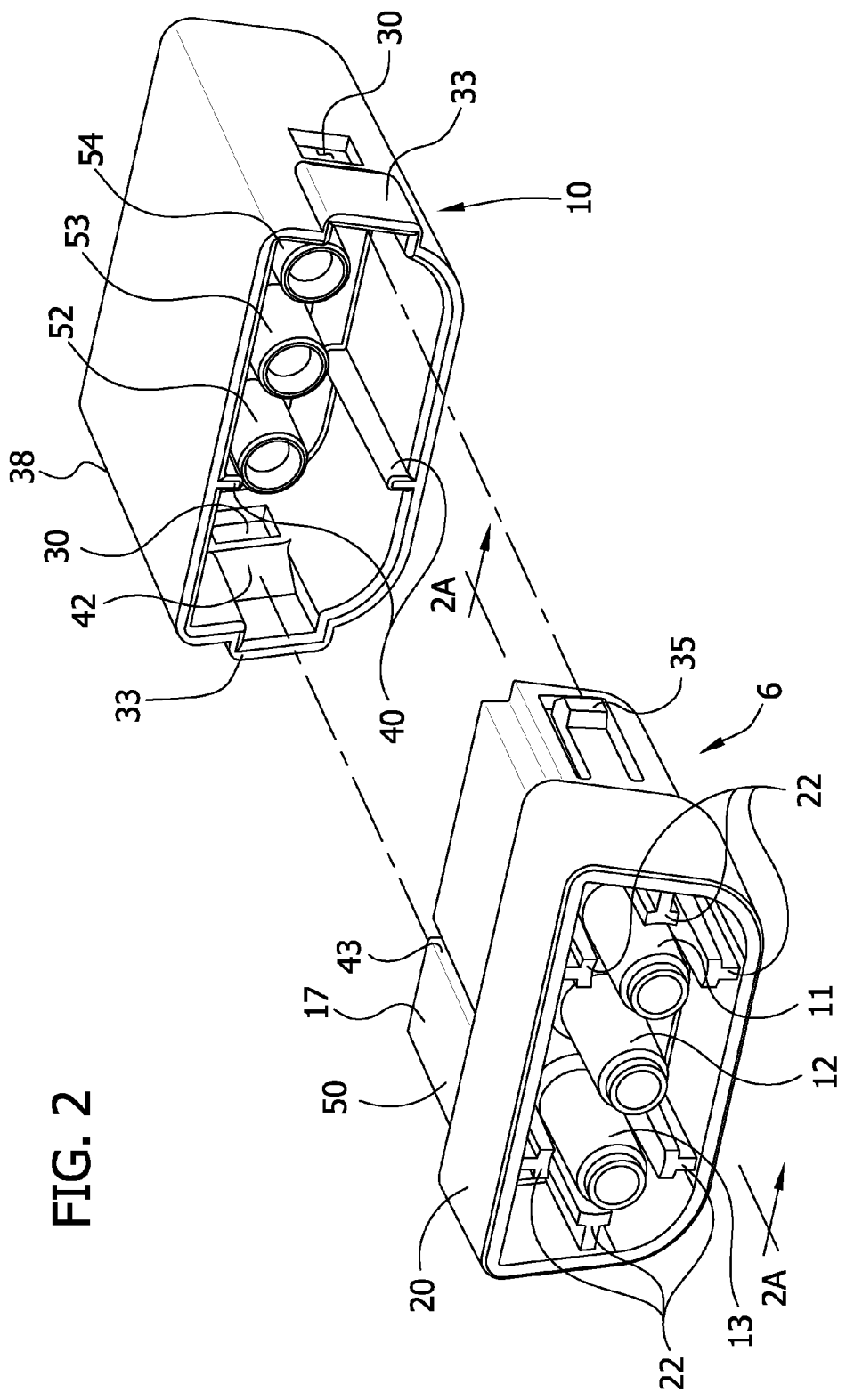
FIG. 2 is a perspective of the connector apparatus of FIG. 1 with the first and second connectors separated.
Figure 2A:
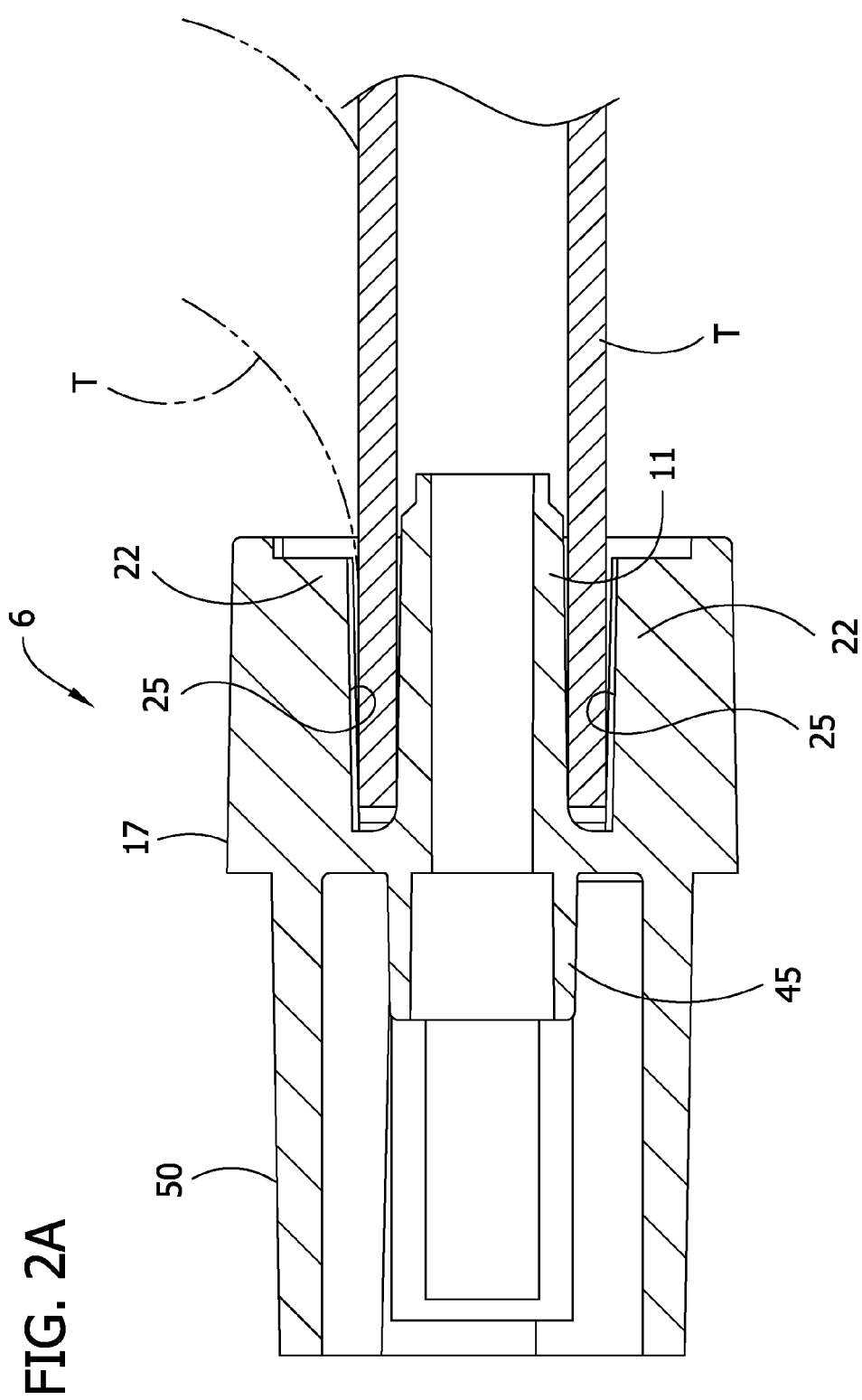
FIG. 2A is a section taken in the plane including line 2A-2A of FIG. 2 and illustrating a flexible tube attached to a tube port of the first connector.

Referring now to the drawings, and in particular FIGS. 1 and 2, a connector apparatus constructed according to principles of the present invention is generally shown at 1. The connector apparatus 1 includes a first connector 6 and second connector 10.

The first connector 6 includes a housing 17 (broadly, "a body") and three tube ports 11,12,13 for attaching flexible tubes (not shown). The tube ports 11,12,13 are sized and shaped for being received in an end of a flexible tube to establish fluid communication between with the flexible tube and the tube port. The tube ports 11,12,13 project along an axis and have an exterior surface suitable for forming a seal with an interior surface of the flexible tube.

The housing 17 includes a shroud 20 which projects outwardly from the housing. The shroud 20 generally surrounds the tube ports 11,12,13. Retainers 22 project from the shroud 20 in a radial direction toward the outer two tube ports 11,13 to restrain lateral movement of the flexible tube with respect to the tube ports 11,13 as will be described more fully hereinafter. Restrain lateral movement may include permitting some limited lateral movement of the tube. Moreover, the restrainers may or may not contact the flexible tube before some lateral movement of the tube on the tube port.

The first connector 6 comprises two resilient latches 35 (one on each side of the first connector) for connection of the first connector and the second connector 10. The second connector 10 includes a housing 38 and connector ports 52,53,54 formed as one piece with the housing. The second connector 10 includes two latch receiving members 33 and mating catch holes 30. The latch receiving members 33 include deflecting portions 42 for deflecting respective resilient latches 35 inward so that ears at the distal ends of the latches can be received within the catch holes 30 upon connection of the first connector 6 and second connector 10. This releasably secures the first and second connectors 6, 10 together. The ears can be manually deflected out of the catch holes 30 to release the connectors 6,10 from each other. Other constructions for releasably securing the first and second connectors together may be used. Moreover, structure for locking the connectors together may be omitted without departing from the scope of the present invention.

In the illustrated embodiment, the connectors 6,10 are keyed to require a predetermined orientation of the first and second connectors where connected. Two guide rails 40 extend from the housing 38 of the second connector 10 for alignment of the first connector 6 and the second connector. The guide rails 40 are adapted to be slidingly received within two corresponding grooves 43 (one shown) of the first connector 6. The rails 40 and grooves 43 guide the connectors 6, 10 straight together upon connection. Moreover, the exterior shapes of the portion of the housing 17 of the first connector 6 (i.e., male portion 50) and the portion of the second connector housing 38 receiving the male portion are also shaped to require a particular orientation of the connectors 6, 10 for connection. Other configurations for alignment and orientation may be used, or the connectors may have no alignment or guidance features within the scope of the present invention.

Figure 3:
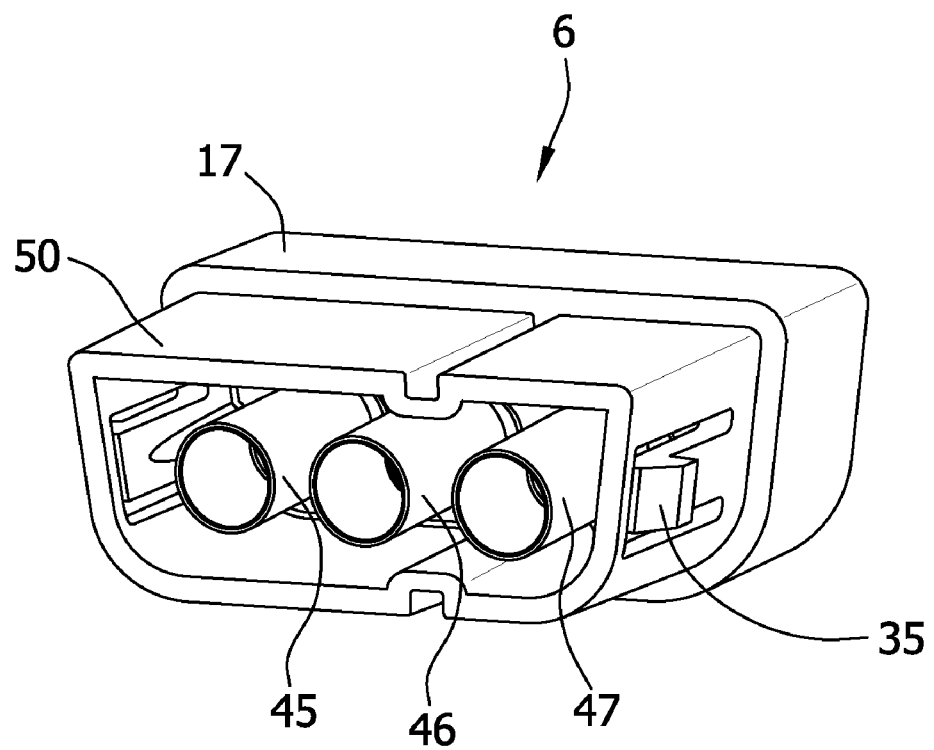
FIG. 3 is a perspective of a mating side of the first connector of FIGS. 1 and 2.

Referring now to FIG. 3, three connector ports 45, 46, 47 are formed as one piece with the housing 17. The connector ports 45, 46, 47 are sized and shaped for connecting the connector ports in fluid communication with the fluid passage of an object such as the connector ports 52,53,54 of the second connector 10. The connector ports 45, 46, 47 are in fluid communication with the tube ports 11,12,13 of the first connector 6. The housing 17 includes the male portion 50, which is sized and shaped to be received in the second connector 10.

Figure 4:
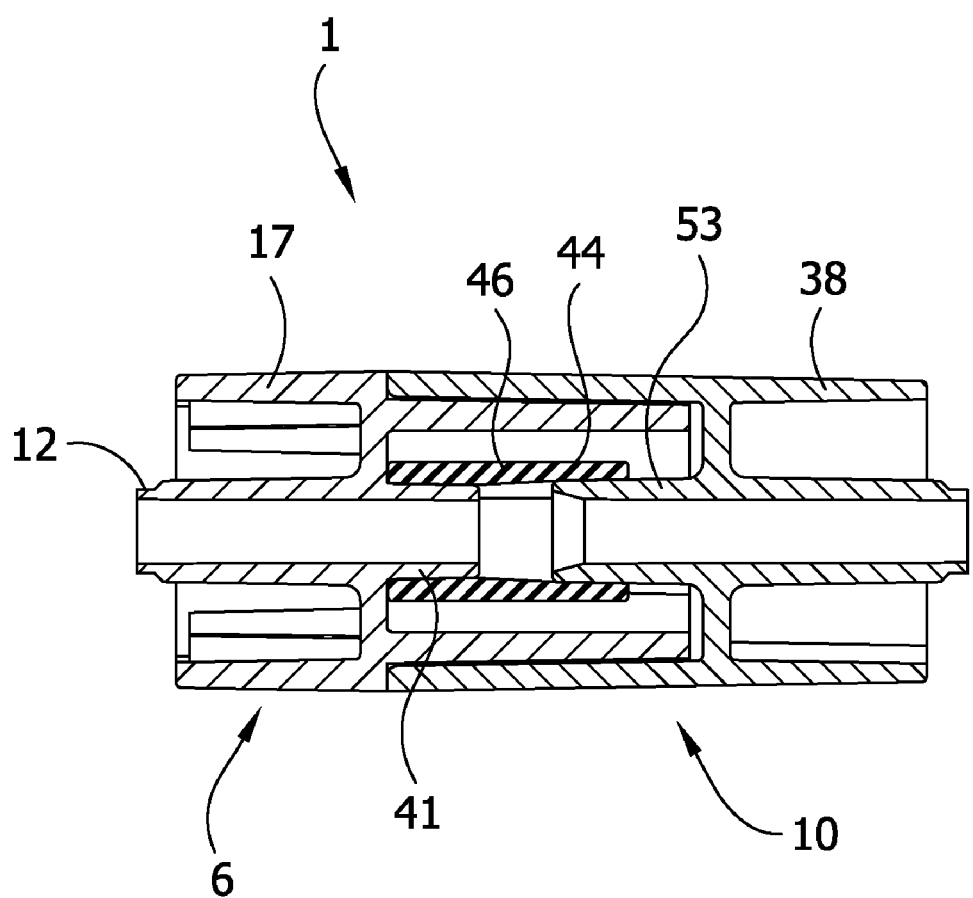
FIG. 4 is a cross sectional view of the connector apparatus of FIG. 1 taken in a plane including line 4-4 on FIG. 1.

The section of the mated first and second connectors 6, 10 shown in FIG. 4 passes through connector port 46 of the first connector 6. The connector port 46 includes a port stem 41 and a gasket 44 attached to the port stem. The gasket 44 may be made of any material sufficient to provide a fluid-tight seal with the connector port 53 such as polyvinylchloride (PVC). The gasket 44 may be attached to the port stem 41 in a suitable manner such as by adhesive. Other constructions for achieving a fluid tight connection of the connector ports 45, 46, 47 of the first connector 6 with the connector parts 52, 53, 54 of the second connector 10 may be used within the scope of the present invention.

To connect the first connector 6 and the second connector 10, the guide rails 40 are aligned with the grooves 43 and force is applied such that the housing 17 of the first connector 6 is received within the housing 38 of the second connector 10 (see, FIG. 2). During connection, the connector ports 45,46, 47 of the first connector 6 (FIG. 3) receive the connector ports 52,53,54 of the second connector 10. The resilient latches 35 are received within the latch receiving members 33. The resilient latches 35 are forced inward by the deflecting portions 42 (only one is shown) of the latch receiving members 33. The housing 17 of the first connector 6 advances into the housing 38 of the second connector until the resilient latches 35 are received within the mating cavities 30 to secure the connectors together.

Figure 5:
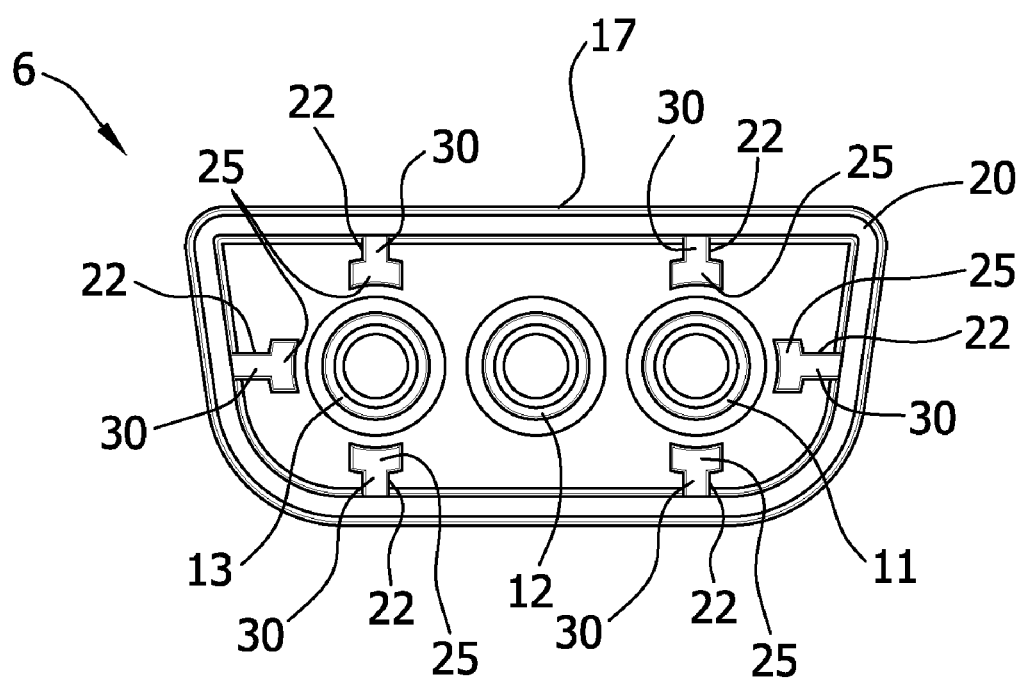
FIG. 5 is a front elevation of the first connector of FIG. 1.

Referring to FIG. 5, the first connector 6 is shown in detail. Each tube retainer 22 comprises a rib 30 which projects from the shroud 20 toward the tube ports 11,13. The retainers 22 also include an engaging end portion 25 attached to each rib 30 and disposed in relation to the tube ports 11,13. Each rib 30 is relatively thin and is generally coextensive with the adjacent tube port (11 or 13). The engaging portion 25 (broadly, "engaging portion member") extends generally transversely to the rib 30 so that, as seen end on in FIG. 5, the retainer 22 has a generally "T" shaped configuration. Other configurations are permitted, but this embodiment provides material savings while also being sufficiently robust. The engaging end portions 25 are in radially opposed relation with a portion of the exterior surface of the tube ports 11,13. The engaging end portions 25 engage the flexible tubes (or are located in close proximity to the flexible tubes) when the tube ports 11,13 are received in the flexible tubes to restrain the flexible tubes from lateral movement with respect to the tube ports.

The retainers 22 are in radially opposed relation to the tube ports 11,13 along the entire axis of the tube ports (FIG. 2). It is within the scope of the present invention that the retainers may be in radially opposed relation to the tube ports along less than the entire axis of the tube ports, however, it is preferred that the retainers oppose the tube ports at least at the distal end of the tube ports in order to prevent forces being applied to the tube ports that would result in separation of the tube port from the connector housing. Moreover, the number of the retainers and the arrangement may be other than illustrated. For instance, the center port 12 is shown as having no corresponding retainers, as the engagement of the tube on the center port 12 with the tubes on either side would restrain the tubes on the center port from substantial lateral movement. However, retainers (not shown) could be positioned next to the center port 12 also. Engaging end portions 25 generally have an arcuate rounded surface. However, the engaging end portions 25 may form a variety of shapes and surfaces for engaging the flexible tube within the scope of the present invention.

Figure 6:
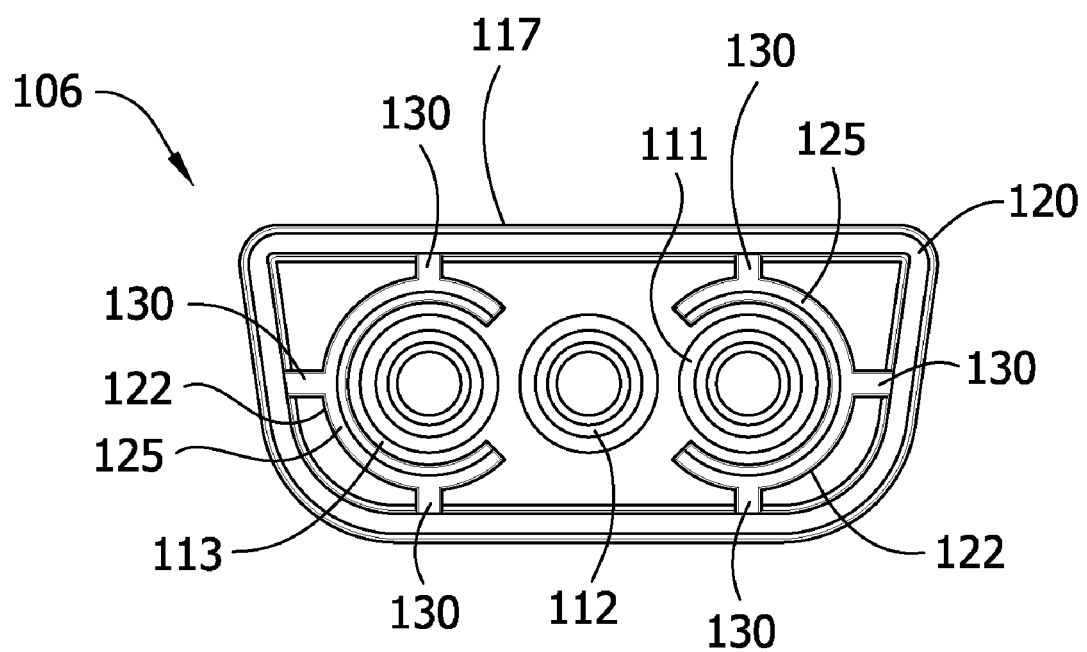
FIG. 6 is a front elevation of a second embodiment of a connector.

Referring now to FIG. 6, engaging end portions 125 of retainers 122 of connector 106 have the shape of a cylindrical segment. The connector 106 is similar to the connector 6, and corresponding parts of the connector 106 will be designated by the same reference numbers as connector 6, plus "100". Ribs 130 extend from the shroud 120. The ribs 130 are spaced apart to effectively support the engaging end portions 125 and each engaging end portion extends continuously between three ribs. Generally speaking, a shape of the end portion 125, whether a shorter arc like end portion 25 or a cylindrical segment 125, that corresponds to the shape of the tube to be engaged by the end portion is preferred.

The first connector 6, 106 can be mated to objects other than the second connector 10 without departing from the scope of the present invention. In embodiments where the first connector 6 is adapted to be mated to the second connector 10, the second connector can be in fluid communication with a variety of objects including a controller 290 of a compression therapy device (FIG. 7) or a tube set 380 (FIG. 8).

Figure 7:
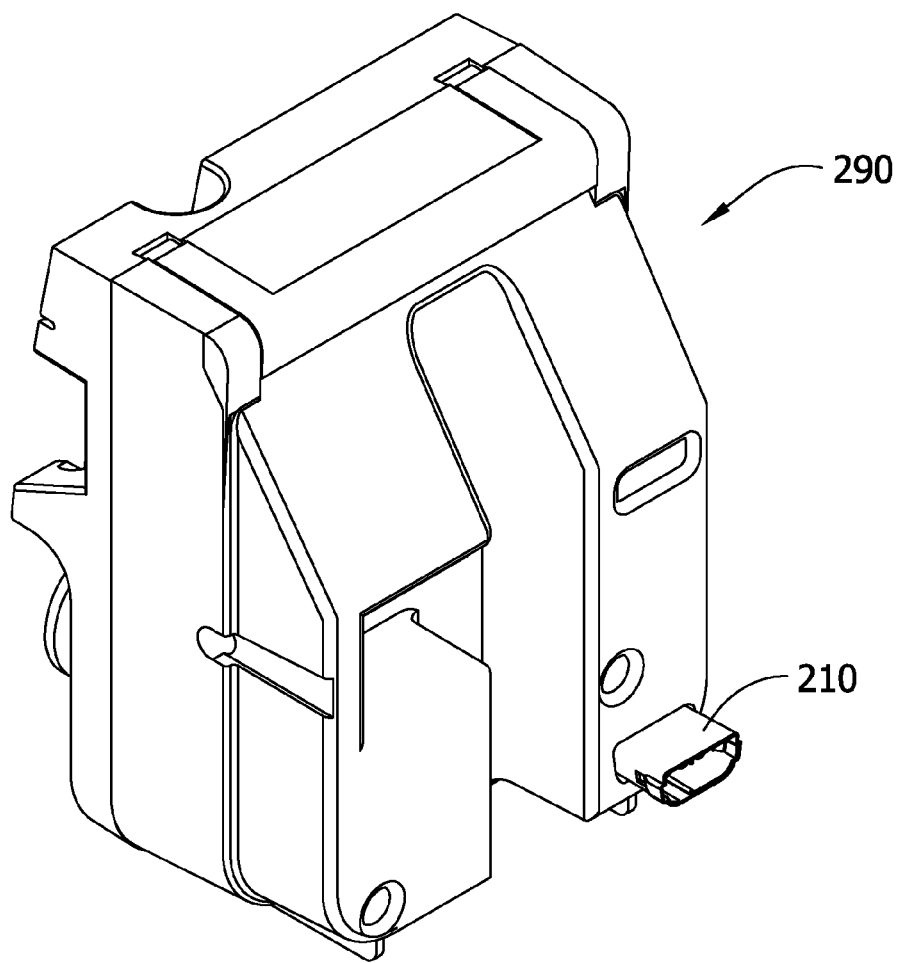
FIG. 7 is a perspective of a controller of a compression therapy device incorporating the second connector of FIG. 2.

Referring to FIG. 7, the controller 290 of a sequential compression therapy device includes a second connector 210 which is in fluid communication with a source of pressurized air. The second connector 210 may have substantially the same configuration as the connector 10. The pressurized air is generated by a pump within the controller 290. The connector 210 is adapted for receiving the first connector 6 illustrated in FIG. 1, or the connector 106 of FIG. 6.

Figure 8:
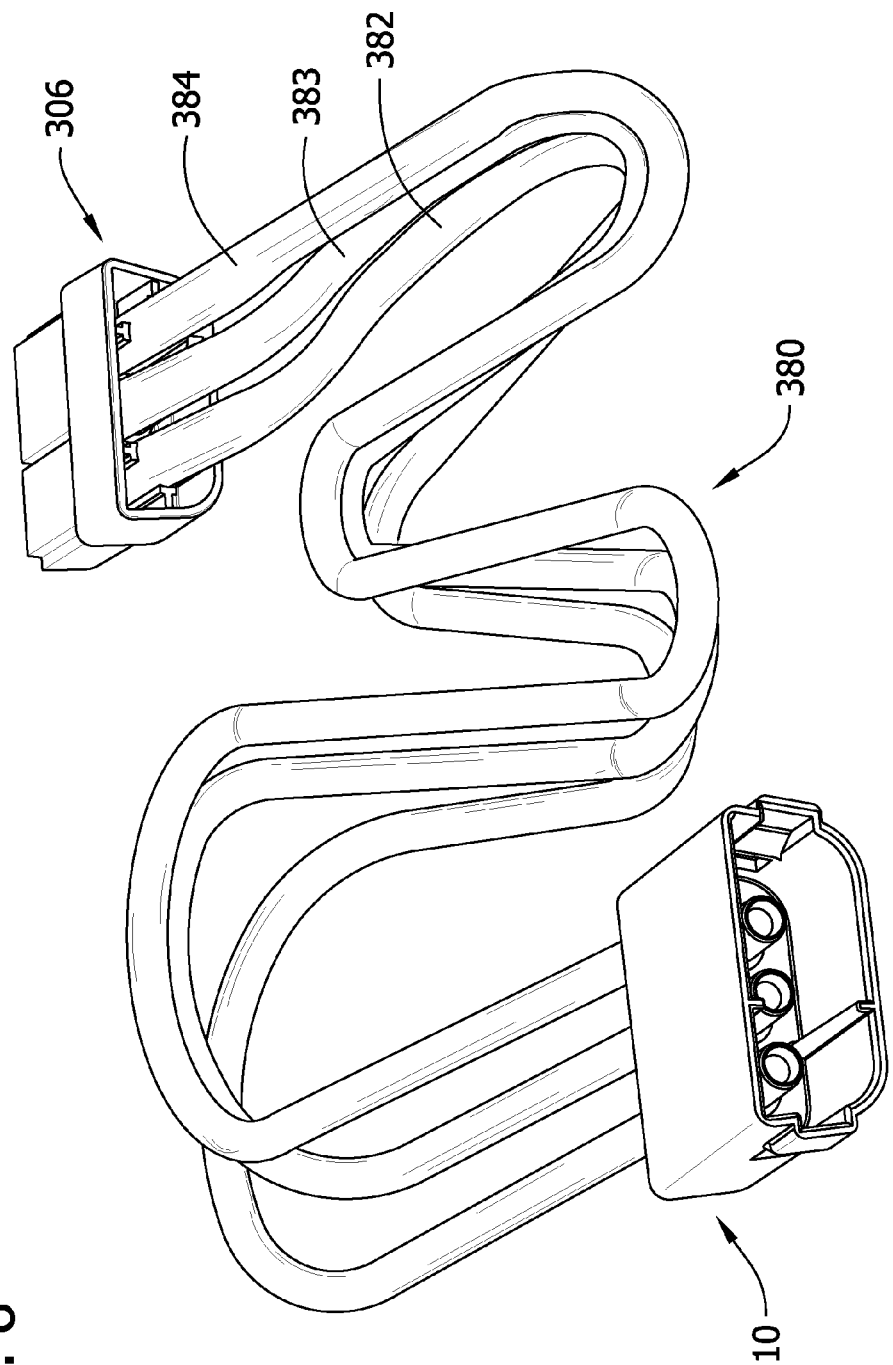
FIG. 8 is a perspective of a tube set including a first connector and a second connector.

Referring to FIG. 8, the tube set 380 is illustrated. The tube set is capable of interconnecting the controller 290 (FIG. 7) with a compression therapy device such as a compression therapy device for application to the leg. The tube set 380 comprises three tubes 382, 383, 384. The first connector 306 includes three tube ports 311, 312, 313 attached to the three tubes 382, 383, 384. The first connector 306 is also adapted for connection to the controller 290 (FIG. 7) of a compression therapy device.

The second connector 310 is attached to the three tubes 382, 383, 384 at opposite ends of the tubes from the first connector 306. The second connector 310 may be adapted for connection to a compression therapy device, for example a compression therapy device for application to the leg as shown and disclosed in U.S. Publ. No. 2005/0187503. The first and second connectors 306, 310 of the tube set 380 correspond to the first and second connectors 6, 10 of FIGS. 1-5.

The first connectors 6, 106 illustrated in FIGS. 5 and 6 include retainers 22, 122 which restrain the flexible tubes attached to the outer two tube ports 11, 13, 111, 113. The first connector 6, 106 may be configured to restrain any number of flexible tubes including each flexible tube attached to the connector or only one of the flexible tubes attached to the connector within the scope of the present invention. Connectors with greater or fewer than three tube ports are also contemplated.

Figure 9:
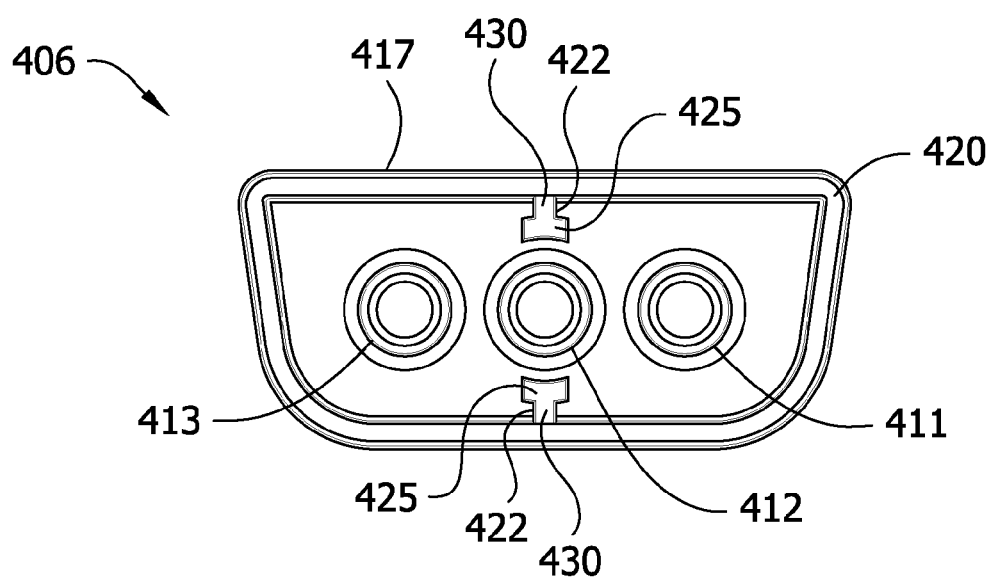
FIG. 9 is a front elevation of a third embodiment of a connector.
Figure 10:
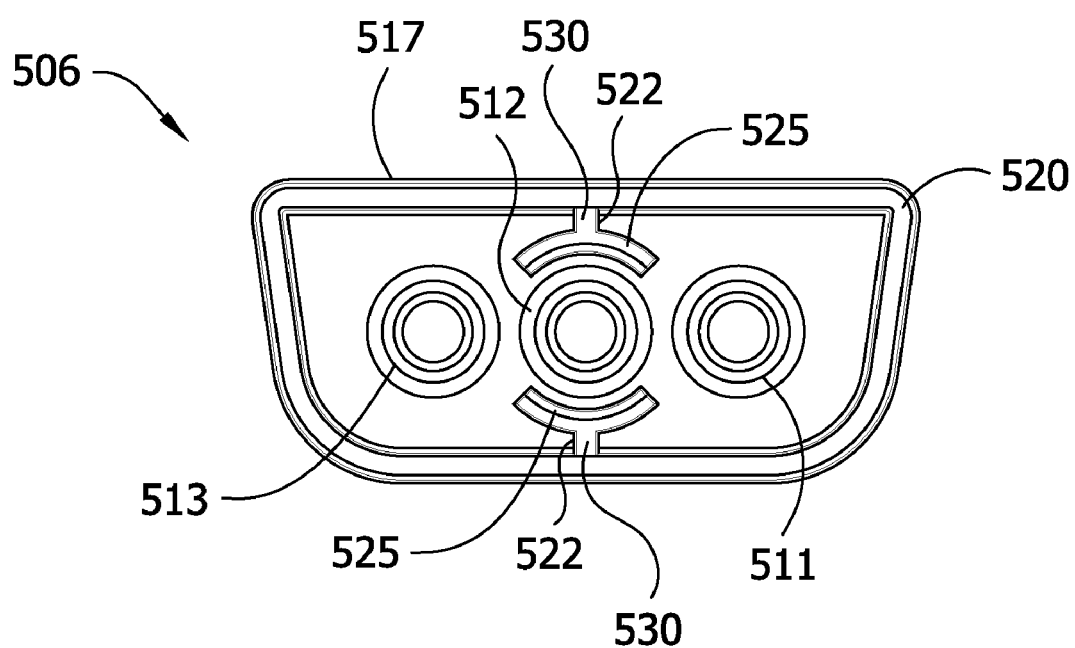
FIG. 10 is a front elevation of a fourth embodiment of a connector.

Referring now to FIG. 9, a first connector 406 includes a middle tube port 412 with retainers 422 disposed in relation to the tube port 412. Except as described, the construction of the first connector 406 is substantially the same as connector 6, and corresponding parts of the first connector 406 are given the same reference number as for connector 6, plus "400." The retainers 422 comprise ribs 430 which project from the shroud 420 and engaging end portions 425 that restrain the flexible tube from lateral movement with respect to the tube port 412. Referring to FIG. 410, a first connector 406 includes a middle tube port 412 with retainers 422 disposed in relation to the tube port 412. The retainers 422 comprise ribs 430 which project from the shroud 420 and arcuate engaging end portions 425 that restrain the flexible tube from lateral movement with respect to the tube port 412.

Figure 11:
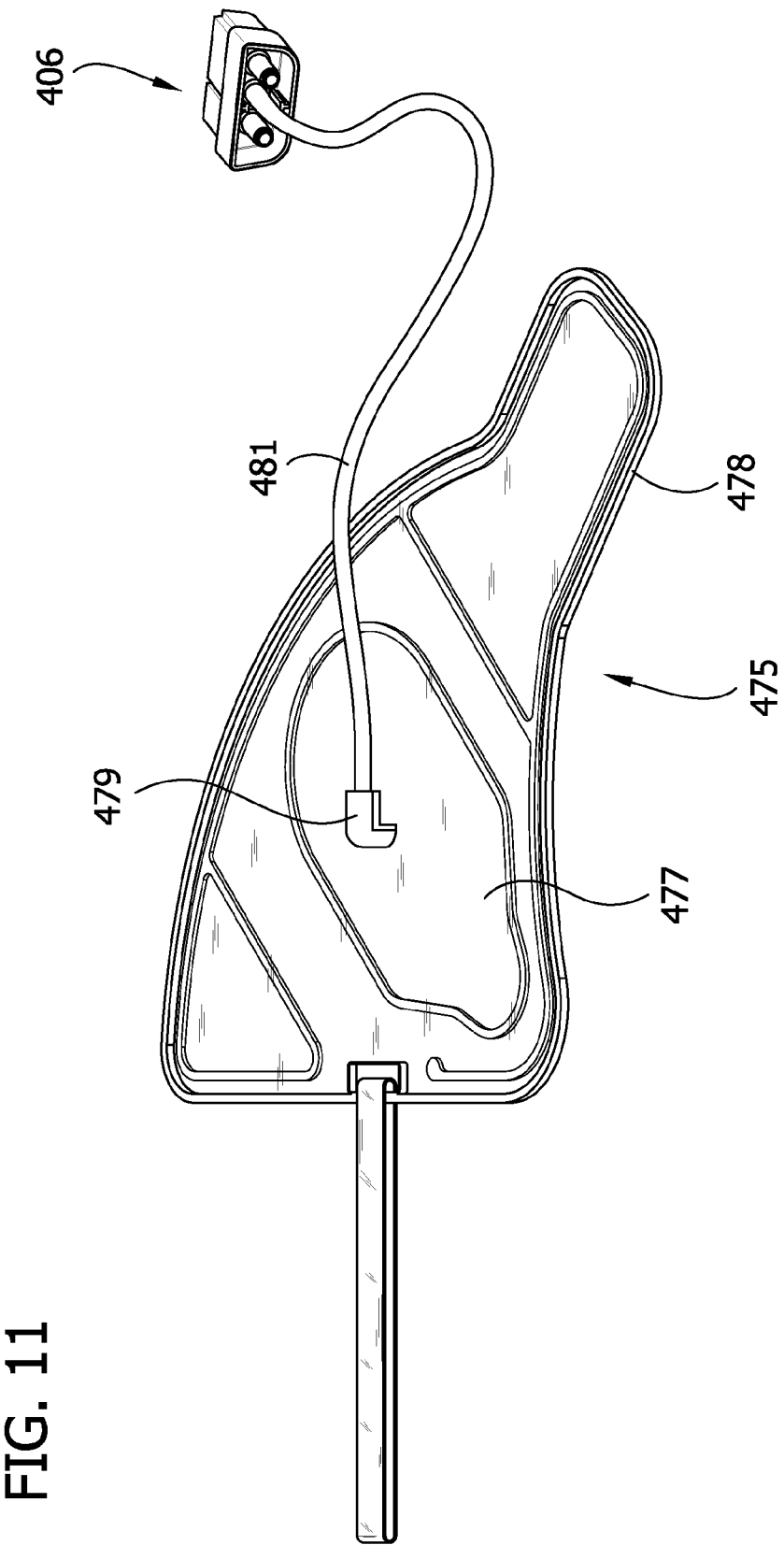
FIG. 11 is a perspective of a compression therapy device including the connector of FIG. 9.

Referring now to FIG. 11, a compression therapy device for use with a source of air pressure includes a bladder 477 located with a wrap 478 sized and shaped for being applied to the foot. The compression therapy device 475 includes a bladder connector 479 for fluid communication between the bladder 477 and a flexible tube 481. The flexible tube is connected at one end to the first connector 406. The first connector 406 is illustrated in detail in FIG. 9 and includes retainers 422 to restrain the flexible tube 481 from lateral movement with respect to the tube port. The first connector 406 is adapted to be releasably secured to a source of air pressure such as the second connector 210 of the controller 290 illustrated in FIG. 7 or the second connector 310 of the tube set 380 illustrated in FIG. 8.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying figures shall be interpreted as illustrative and not in a limiting sense.

What is claimed is:

1. A connector for attaching at least one flexible tube to a fluid passage of another object, the connector comprising a body, at least one connector port on the body sized and shaped for connecting the connector port in fluid communication with the fluid passage of the object, at least one tube port projecting from the body adapted for fluid communication with the connector port, the tube port being sized and shaped for being received in an end of the flexible tube to establish fluid communication with the flexible tube, and a tube retainer projecting from the body toward the tube port and having an engaging end portion disposed in relation to the tube port to engage the flexible tube when the tube port is received in the flexible tube to restrain the flexible tube from lateral movement with respect to the tube port, wherein the tube retainer comprises at least one rib projecting from the body.

2. A connector as set forth in claim 1 wherein the tube port projects along an axis and has an exterior surface, the end portion of the tube retainer being in radially opposed relation with at least a portion of the exterior surface of the tube port.

3. A connector as set forth in claim 2 wherein the tube retainer is in radially opposed relation with a distal end portion of the tube port.

4. A connector as set forth in claim 3 wherein the engaging portion has an arcuate surface.

5. A connector as set forth in claim 4 wherein the engaging portion has the shape of a cylindrical segment.

6. A connector as set forth in claim 1 wherein the tube retainer comprises plural, spaced apart ribs projecting from the body.

7. A connector as set forth in claim 6 wherein the engaging portion extends continuously between the ribs.

8. A connector as set forth in claim 6 wherein the engaging portion comprises separate engaging portion members each being associated with a respective one of the ribs.

9. A connector as set forth in claim 1 wherein the body comprises a shroud projecting outwardly from the body and generally surrounding the tube ports, the rib projecting from the shroud.

10. A connector as set forth in claim 1 further comprising plural tube ports and plural tube retainers.

11. A connector as set forth in claim 1 in combination with the flexible tube receiving the tube port therein.

12. A compression system for use in applying pressure to an appendage of a patient comprising:
an air pump for supplying air under pressure and having a fluid passage;
at least one flexible tube;
a connector adapted for attachment to an outlet of the air pump and for attaching said at least one flexible tube to a fluid passage of another object, the connector comprising a body, at least one connector port on the body sized and shaped for connecting the connector port in fluid communication with the fluid passage of the air pump, at least one tube port projecting from the body adapted for fluid communication with the connector port, the tube port being sized and shaped for being received in an end of the flexible tube to establish fluid communication with the flexible tube, and a tube retainer projecting from the body toward the tube port and having an engaging end portion disposed in relation to the tube port to engage the flexible tube when the tube port is received in the flexible tube to restrain the flexible tube from lateral movement with respect to the tube port, wherein the tube retainer comprises at least one rib projecting from the body.

13. A compression system as set forth in claim 12 in combination with the object, the object comprising a compression therapy device adapted for operative connection to the air pump by way of the flexible tube, the compression therapy device having at least one bladder therein for receiving air from the air pump.

14. A compression system as set forth in claim 13 wherein the tube port projects along an axis and has an exterior surface, the end portion of the tube retainer being in radially opposed relation with at least a portion of the exterior surface of the tube port.

15. A compression system as set forth in claim 14 wherein the tube retainer is in radially opposed relation with a distal end portion of the tube port.

16. A compression system as set forth in claim 15 wherein the engaging portion has an arcuate rounded surface.

17. A compression system as set forth in claim 16 wherein the engaging portion has the shape of a cylindrical segment.

18. A compression system as set forth in claim 12 wherein the tube retainer comprises plural, spaced apart ribs projecting from the body.

19. A compression system as set forth in claim 18 wherein the engaging portion extends continuously between the ribs.

20. A compression system as set forth in claim 18 wherein the engaging portion comprises separate engaging portion members each being associated with a respective one of the ribs.

21. A compression system as set forth in claim 18 wherein the body comprises a shroud projecting outwardly from the body and generally surrounding the tube ports, the rib projecting from the shroud.

22. A compression system as set forth in claim 12 further comprising plural flexible tubes, plural tube ports and plural tube retainers.

23. A compression therapy device for use with a source of air pressure having a fluid passage, the compression therapy device comprising at least one air bladder sized and shaped for being applied to an appendage of a patient and in fluid communication with a flexible tube, a connector connected to the tube, the connector comprising a body, at least one connector port on the body sized and shaped for connecting the connector port in fluid communication with the fluid passage of the source of air pressure, at least one tube port projecting from the body adapted for fluid communication with the connector port the tube port being sized and shaped for being received in an end of the flexible tube to establish fluid communication with the flexible tube, and a tube retainer projecting from the body toward the tube port and having an engaging end portion disposed in relation to the tube port to engage the flexible tube when the tube port is received in the flexible tube to restrain the flexible tube from lateral movement with respect to the tube port, wherein the tube retainer comprises at least one rib projecting from the body.

24. A compression therapy device as set forth in claim 23 wherein the compression therapy device comprises a bladder sized and shaped for being applied to the foot.

25. A compression therapy device as set forth in claim 23 wherein the tube port projects along an axis and having an exterior surface, the end portion of the tube retainer being in radially opposed relation with at least a portion of the exterior surface of the tube port.

26. A compression therapy device as set forth in claim 25 wherein the tube retainer is in radially opposed relation with a distal end portion of the tube port.

27. A compression therapy device as set forth in claim 26 wherein the engaging portion has an arcuate surface.

28. A compression therapy device as set forth in claim 27 wherein the engaging portion has the shape of a cylindrical segment.

29. A compression therapy device as set forth in claim 23 wherein the tube retainer comprises plural, spaced apart ribs projecting from the body.

30. A compression therapy device as set forth in claim 29 wherein the engaging portion extends continuously between the ribs.

31. A compression therapy device as set forth in claim 29 wherein the engaging portion comprises separate engaging portion members each being associated with a respective one of the ribs.

32. A compression therapy device as set forth in claim 29 wherein the body comprises a shroud projecting outwardly from the body and generally surrounding the tube ports, the rib projecting from the shroud.

33. A compression therapy device as set forth in claim 23 further comprising plural flexible tubes, plural tube ports and a tube retainer for each tube port.

* * * * *